United States Patent [19]

Köhler

[11] Patent Number: 5,068,228

[45] Date of Patent: Nov. 26, 1991

[54] USE OF A METAL CHELATE OF AN ALKYLAMINOESTER OF PHOSPHORIC ACID FOR PROPHYTLAXIS OR THERAPY OF A NEUROPATHY

[76] Inventor: Gernot Köhler, Neue Bergstrasse 3 - 7, 6146 Alsbach-Hähnlein, Fed. Rep. of Germany

[21] Appl. No.: 231,015

[22] Filed: Aug. 11, 1988

[30] Foreign Application Priority Data

Aug. 11, 1987 [DE] Fed. Rep. of Germany ....... 3726721

[51] Int. Cl.$^5$ ...................... A01N 57/10; A61K 31/66
[52] U.S. Cl. ........................................ 514/114; 514/76
[58] Field of Search ....................... 514/76, 79, 80, 81, 514/114

[56] References Cited

PUBLICATIONS

"Effects of Feeding Organic or Inorganic Zinc Compounds on Rate of Protein Synthesis in Liver and Growth of Rats", Kietzmann, M., DTW, Dtsch. Tieraerztl.Wochenschr., 91 (11–12), 391-2, 395-6.

"Complexes of Copper (II) with 3-Aminopropyl Phosphonic Acid and 0-Phosphoethanolamine", Wozniak, Michel et al., Analysis, 1(7), 498–502.

Durak, H., "Kalzium-Schlepper-Substanzen in der Behandlung von zerebellarataktischen Erscheinungsformen der multiplen Sklerose", Med. Welt 19 (N.F.): 524–527 (1968).

*Primary Examiner*—Thurman K. Page
*Assistant Examiner*—Carlos Azpuru
*Attorney, Agent, or Firm*—Fleit, Jacobson, Cohn, Price, Holman & Stern

[57] ABSTRACT

The use of a metal chelate of an alkylaminoester of phosphoric acid for the prophylactic or therapeutic treatment of, in particular, diabetic neuropathy is described.

25 Claims, No Drawings

USE OF A METAL CHELATE OF AN ALKYLAMINOESTER OF PHOSPHORIC ACID FOR PROPHYTLAXIS OR THERAPY OF A NEUROPATHY

BACKGROUND OF THE INVENTION

The concept of diabetic polyneuropathy encompasses disturbances of the peripheral sensory-motor and autonomous nervous system that manifest themselves by various clinical phenomena. In accordance with this definition, these syndromes are considered to be caused by the diabetic disturbances of the metabolism, the pathogenesis of which, however, is not clear, and which assumes individually varying forms of progress. Accordingly, disturbances of the blood supply by way of the vasa nervorum (microangiopathy) as well as primary disturbances of the metabolism of the nerves and of Schwann cells are assumed to be due to hypoglycemia. Pathological changes of the properties of the membranes, in particular of the neuraxon and/or disturbances of axonal transport and of transmission of signals, are considered to be the cause of the degeneration of the mechanism for the transmission of stimuli. Accordingly, therapeutic formulations represent, on the one hand, attempts to restore the metabolic derailment in the membranes by treating the underlying diabetes, and, on the other hand, attempts to eliminate membrane damage by the substitution of membrane-specific substances, such as myoinositol or gangliosides. The results of a causal therapy depend, however, not only on the formulation of the therapy, but also on the stage of the neuropathy. Especially favorable results are expected prophylactically during an early stage of the disease. As soon as structural defects of considerable extent are present, the beneficial effects of therapeutic formulae become dubious and without any clinical relevance, in-as-much as the neurons+ regenerative capability is limited, and the beneficial effects become futile in cases of advanced polyneuropathy.

Investigations of recent years have demonstrated that, after the onset of diabetes, a decrease in peripheral conduction velocity occurs when the diabetes was handled poorly. In the case of patients with disturbances of the velocity of the conduction of sensory-motor nerves or of autonomous functions, it was possible to achieve an improvement by an optimal adjustment of the metabolism. The optimalization of the metabolic condition is considered the essential basis of treatment of any form of diabetic polyneuropathy. The restoration of normal functions is, however, rarely possible and even less possible when the polyneuropathy is in an advanced state.

The findings concerning pathological changes of the systems of stimulus-conduction in diabetes, as presented herein, are comparable, as to their clinical manifestations, to numerous other neuropathies whose genesis derives from pathological changes of the nerve cells, in particular of the axon, and which reduce the velocity of stimulus conduction. Neuropathies of this type are, e.g., diabetogenic neuropathy, funicular myelosis, carcinogenic neuropathy, alcoholic polyneuropathy, neuropathies after long-term cytostatic therapy, dysglobulinemic neuropathy, myelo-optical neuropathy, encephalitis periaxialis concentrica, subacute sclerosing panencephalitis, as well as presbyophrenic cerebral dysfunctions, such as Alzheimer's disease.

OBJECT OF THE INVENTION

This invention provides substances that can be used as effective pharmaceutical products for the prophylactic and therapeutic treatment of the aforementioned neuropathies. The administration of these substances within the prescribed dosage is free of side-effects.

SUMMARY OF THE INVENTION

The effective substances of the invention consist of a group of compounds that are herein designated as a metal chelates of alkylamino-esters of phosphoric acid and have the following general structural formula:

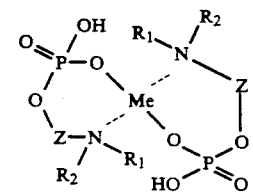

In this structural formula, Me designates an alkaline earth metal or transition metal, comprising calcium, magnesium, zinc, copper, iron, and manganese, while $R_1$ and $R_2$ each designate a hydrogen atom, a lower alkyl radical (n=1, 2) or a combination of both, Z designates a lower alkyl radical with straight or branched chain (n=1, 2, 3, 4), a monocarboxylic acid (n=2, 3, 4), or a combination of an alkyl radical and a monocarboxylic acid, and n indicates the number of carbon atoms.

In particular, the following effective substances of the aforementioned group of substances are proposed for treatment and prophylaxis of neuropathies in accordance with the invention:

Calcium-di (2-aminoethylphosphate), abbreviated as Ca-EAP, magnesium-di(2-aminoethylphosphate), abbreviated as Mg-EAP, zinc-di(2-aminoethylphosphate), abbreviated as Zn-EAP, calcium-di(2-N-methylaminoethylphosphate), abbreviated as Ca-EAMP, magnesium-di(2-N-methylaminoethylphosphate), abbreviated as Mg-EAMP, calcium-di(2-N, N-dimethylaminoethylphosphate, abbreviated as Ca-DMAP, magnesium-di(2N, N-dimethylaminoethylphosphate), abbreviated as Mg-DMAP, calcium -di( -serylphosphate), abbreviated as Ca-ASP, magnesium-di( serylphosphate), abbreviated as Mg-ASP, calcium-di( threonylphosphate), abbreviated as Ca-PTE, magnesium-di( threonylphosphate), abbreviated in the following as Mg-PTE.

SPECIFIC EMBODIMENTS OF THE INVENTION

In the following, examples of the methods of producing the aforementioned compounds will are presented.

EXAMPLE 1

Production of phosphoric acid-mono-(2-aminoethylester) (EAP)

Generally: A good yield results from the phosphorylation of 2-hydroxy-ethyl amine with polyphosphoric acids. This reaction does not result in any phosphoric acid amine linkage. By the use of other methods condensation and phosphorylation may occur to the same extent so that bis-and tris-2-hydroxyethyl amines are produced from which phosphorylated hydroxyl-morphine and/or piperazines are formed.

Under refrigeration, 2-hydroxyethyl amine is mixed with a residue of polyphosphoric acid and heats the mixture slowly, over several hours, to 100° C.

Specifically: Under refrigeration, 0.2 mol 2-hydroxyethyl amine are added to 0.1 mol polyphosphoric acid. After spontaneous heating has come to an end, the mixture is heated, over a period of some 4 hours, to 100° C. The reaction mixture is placed in water and neutralized by the addition of an alkaline earth carbonate. The salt precipitate is filtered out and washed, and the filtrate is evaporated in a vacuum. By repeated solution and with subsequent concentration, the free phosphoric acid-mono-aminoethylester is isolated. Phosphoric acid-mono-(2-amino-ethylester) B.p.: 237° C. Complex formation to Ca-EAP.

Generally: The ester obtained in accordance with the above procedure is dissolved in an alkaline solution and adjusted to pH 10 with calcium hydroxide. After the reaction, carbon dioxide is added, to neutralize the solution, calcium phosphate and/or calcium carbonate is filtered out, and the filtrate is concentrated by evaporation. By means of adding ethanol, the desired product is precipitated.

Specifically: 100 g of phosphoric acid-mono-(2-aminoethyl ester) are added to an aqueous solution with 2 g sodium hydroxide. At approximately 30° C., 50 g calcium hydroxide are added, and the pH value is adjusted to 10. The reaction mixture is heated to 50° C. and allowed to react for some 20 minutes. After cooling, carbon dioxide is added for the neutralization of the reaction mixture, and the precipitated calcium phosphate and/or calcium carbonate is filtered out. The filtrate is reduced and 100 ml alcohol are added; in that way, the end product may be filtered. The yield will amount to some 100 g, i.e., a yield of 88%.

| Analysis: Ca—EAP $C_4H_{14}O_8N_2P_2Ca$ MW: 320.2 | | |
|---|---|---|
| | theor. % | 1st % |
| C | 15,00 | 14,94 |
| H | 4,41 | 4,54 |
| N | 8,75 | 8,82 |
| Ca | 12,52 | 12,30 |

Mg-EAP is obtained by the method as described above for Ca-EAP; magnesium hydroxide is added instead of calcium hydroxide.

| Mg—EAP $C_4H_{14}O_8N_2P_2Mg$ MW: 304.42 | | |
|---|---|---|
| | theor. % | 1st % |
| C | 15.78 | 16.01 |
| H | 4.64 | 4.97 |
| N | 9.20 | 9.47 |
| Mg | 7.98 | 7.66 |

EXAMPLE 2

Preparation of phosphoric acid-mono-(2-dimethylamino-ethyl ester) DMAP

The synthesis of DMAP takes place analogously to Example 1, but here, a reaction temperature of 80° C. is sufficient.

Under refrigeration, 0.2 mol 2-hydroxyethyl-dimethylamine are gradually added to 0.1 mol polyphosphoric acid. After spontaneous heating has come to an end, the mixture is heated to 80° C. over a period of some 4 hours. The reaction mixture is placed in water and neutralized by the addition of an alkaline earth carbonate. The salt precipitate is filtered off and washed; the filtrate is evaporated in a vacuum. Purification takes place analogously to Example 1. Phosphoric acid-mono-(2-dimethylamino-ethyl ester) BP: 80° C.

Complex formation for Ca-DMAP. The ester obtained in accordance with the method described above is complexed analogously to the method described in Example 1. The yield amounts to 75%.

| Analysis: Ca—DMAP $C_8H_{22}O_8N_2P_2Ca$ MW: 376.3 | | |
|---|---|---|
| | theor. % | 1st % |
| C | 25,54 | 25,37 |
| H | 5.89 | 6,10 |
| N | 7,44 | 7,31 |
| Mg | 10,65 | 10,42 |

Analogously, the magnesium complexes may be prepared; the following analysis value are the result:

| Mg—DMAP $C_8H_{22}O_8P_2Mg$ MW: 360.529 | | |
|---|---|---|
| | theor. % | 1st % |
| C | 26,65 | 26,58 |
| H | 6,15 | 5,99 |
| N | 7,77 | 7,72 |
| Mg | 6,74 | 6,86 |

EXAMPLE 3

Preparation of calcium-di-(serylphosphate) (Ca-ASP)

50 g serine are placed in 250 g phosphoric acid. At a reaction temperature of 80° C. for a period of 30 minutes, the mixture is allowed to react. Subsequently, at a constant temperature (80° C.), 100 ml 2 n HCl solution are added slowly, and the phospho-serine ester is precipitated with a mixture of 700 ml acetone and 250 ml ether. The settled compound is again dissolved in 200 ml water, mixed with some 170 ml ethanol, whereupon the compound crystallizes out slowly. The yield amounts to 79%.

Phospho-threonine ester (PTE) may be synthesized analogously.

Complexation to Ca-ASP, Ca-PTE, Mg-PTE

The syntheses of the complex compounds may be carried out basically in accordance with the method in accordance with Example 1 and 2. The yields are reduced, however, because of the higher solubility of these compounds. When carrying out the reaction, it is advantageous to extend the reaction time and, at the same time, to reduce the temperature. (max. 75° C.), so as to prevent any condensation reactions. After repeated purifications as described, one obtains the following analysis results:

| | theor. % | 1st % |
|---|---|---|
| Ca—ASP $C_6H_{14}O_{12}N_2P_2Ca$ MW: 408.2 | | |
| C | 17,65 | 17,58 |
| H | 3,46 | 3,72 |
| N | 6,86 | 6,77 |

-continued

|  | theor. % | 1st % |
|---|---|---|
| Ca | 9,82 | 9,68 |
| Ca—PTE | | |
| C₈H₁₈O₁₂N₂P₂Ca MW: 436.3 | | |
| C | 22.03 | 22.33 |
| H | 4,16 | 4,37 |
| N | 6,42 | 6,16 |
| Ca | 9,19 | 9,02 |
| Mg—ASP | | |
| C₆H₁₄O₁₂N₂P₂Mg MW: 392.4 | | |
| C | 18.36 | 18.31 |
| H | 3,60 | 3,88 |
| N | 7,14 | 7,06 |
| Mg | 6,19 | 6,41 |
| Mg—PTE | | |
| C₈H₁₈O₁₂N₂P₂Mg MW: 420.5 | | |
| C | 22.85 | 23.05 |
| H | 4,31 | 4,52 |
| N | 6,66 | 6,48 |
| Mg | 5,78 | 6,02 |

For any other details, reference is made to Houben Weyl, vol, 12, II, pages 145 seq.

The therapeutic and prophylactic effectiveness of the active agents in accordance with the structural formula given above is discussed in the following on the basis of the calcium chelates of the ethanol-aminophosphoric acid (Ca-EAP).

The therapeutic efficacy of calcium 2-aminoethyl phosphate for the treatment of tetany and other calcium-deficiency disorders has been known for a long time. Various publications have appeared on this. The active substance has the structural formula:

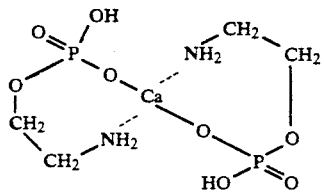

and the UPAC name calcium 2-aminoethyl phosphate (Ca-EAP).

It has been possible to show, on the basis of recent findings, that the active substance is also excellently suitable for the prophylactic or therapeutic treatment of diabetic neuropathy in humans. Diabetic neuropathy is a common sequela of diabetes mellitus; as a rule, it takes the form of diminished visual acuity, impairment of coordination and cerebral retardation. It emerges that a daily dose of calcium 2-aminoethyl phosphate has an outstanding effect on the transmission of impulses via the nerve tracts and, thus, considerably diminishes the diabetic neuropathy.

The pathoanatomical changes in the approximately 50% of diabetics who are prone to neuropathy are diverse and heterogeneous. Thus, there is often disturbance of the axons of the motor cells of the anterior horn, which means that the striped skeletal muscle cannot be sufficiently innervated. The consequences of this are considerable impairments of the locomotor system because of neurogenic muscular atrophy. diabetic microangiopathy, a specific form of perfusion disturbance which may result in loss of the extremities. This takes the form of degeneration of spinal gangliocytes and of degeneration of the posterior white column, resulting in circulation disturbances and vascular lesions. The angiopathy probably contributes to acute monopareses and neuromyopathies but not to the primary changes in the satellite cells and gangliocytes of the anterior horn and spine, since the diffuse neuropathies may develop independently of angiopathies, nephropathies and retinopathies. Reproducible changes in the brain and spinal cord, together with degeneration of the gangliocytes of the anterior horn and spine, have been found after an excessive insulin dose in animal experiments, and have been shown to be unambiguously connected with the neuropathies.

From this it is likewise possible to deduce indications for other neuropathies whose clinical picture, although etiologically different, is attributable to the same pathoanatomical changes. Polyneuropathies following prolonged alcohol abuse derive, in just the same way as neuropathies due to long-term therapy with cytostatics, from the same pathomechanisms as diabetic neuropathy. In the same way, polyneuropathies are commonly seen with carcinomas, especially with bronchial carcinoma. Once again, according to Denny-Brown (J. Neurol. Neurol. Surg. Psychiat. 11 (1984), 73), this takes the form of degeneration of the spinal gangliocytes.

Dysglobulinemic neuropathies are manifested by quantitative shifts in the serum globulins and the occurrence of abnormal macro- and cryoglobulins (paraproteinemia). They are accompanied by diffuse or disseminated neuropathies. Apart from Waldenstrom macroglobulinemia, similar changes are found with reticuloses, or with periarteritis nodosa, with visceral lupus erythematosus, with Reiter syndrome, with thrombotic microangiopathy, with rheumatoid arthritis with abnormal globulins in the serum, with malignant tumors and leukemias, with multiple myeloma and with cirrhosis of the liver.

Clinical experience to date with the active substance, calcium 2-aminoethyl phosphate, in MS patients likewise leads to the conclusion that the therapeutic effect derives from restoration of the demyelinated axons. The remyelinization improves conduction as long as the Ranvier nodes are able to transmit the impulse. The structure and function of the myelin sheath are comparable with those of a condenser which discharges with a stimulus and transmits the impulse to the next switching point (Ranvier node). In this way the impulse is transmitted over several switching points and several myelin sheath segments until it finally innervates the target organ.

The active substance described herein repairs the myelin sheath in such a manner that its condenser action regains complete functioning and the impulse does not "seep away". Assumption of a mechanism of action of this type explains the success of therapy for a large number of so-called demyelinating disorders. The differences in the clinical pictures are the expression of different nerve segments and the organs which they innervate. However, according to the present state of knowledge, the cause of all is the demyelinization whose etiology varies, and is sometimes unknown.

In summary, the therapeutic use of calcium 2-aminoethyl phosphate relates to all clinical pictures associated with a disturbance of the conduction mechanism resulting from changes in the medullary sheath or general or selective demyelinization. The mechanism of action is based on a specific membrane activation by the substrate phosphatidyl-ethanolamine which is a structural element of the active substance. Owing to this affinity of the active substance for nerve cells, the calciumdependent membrane functions are stimulated in an optimal manner.

The dosage of Ca-EAP varies from one case to another and also depends on the clinical picture of the patient. The following dosage has been used successfully: for long-term therapy, an oral administration of daily 2×2 coated pills (each pill contains 350 mg and contains 43.82 mg calcium and conventional galenic medications) and a parenteral administration of 3 ampoules (each ampoule contains 10 ml and 50.08 mg calcium), distributed over one week, preferably on Monday, Wednesday and Friday. Depending on the seriousness of the symptoms, the dosage may be tripled; in this case, clinical-chemical control is indicated. The high dosage should be administered for no more than 2 weeks; subsequently, the suggested dosage for long-term therapy as given above should be applied.

Test on a model of diabetes:

The surprisingly persistent affect of calcium 2-aminoethyl phosphate on the velocity of nerve conduction is evident from the results, which are discussed below, of an investigation on rats with streptozotocin-induced diabetes.

A single injection of 70 mg/kg streptozotocin irreversibly destroys the islet cells of the pancreas and, hence, induces a diabetic status which subsequently gives rise, over the course of four or eight weeks, to peripheral neuropathy. This can be detected electrophysiologically at this time by a decrease in the velocity of nerve conduction.

On the basis of this parameter, a daily subcutaneous injection of calcium 2-aminoethyl phosphate significantly reduces the severity of developing diabetic neuropathy.

The parameters used for detecting the diabetic neuropathy were the conduction velocities (hereinafter CV) in the motor and sensory fibers in the nerve of the rat tail. The experimental method follows that described in the study by Spuler-Dimpfel-Tullner: "Effect of Gangliosides on Nerve Conduction Velocity during Diabetic Neuropathy in the Rat", published in Archives Internationales de Pharmacodynamie et de Therapie, Vol. 287, No. 2, June 1987, pages 211 to 223.

After the first electrophysiological measurement, diabetes was induced in some of the experimental animals by injection of 70 mg/kg streptozotocin. Further determinations of the CV were carried out four and eight weeks after induction of the diabetes.

The experiments were carried out on a total of 59 experimental animals in three experimental groups:

1 The control group of 14 animals (n=14) which received no streptozotocin injection and were not diabetic.

2. The 22 animals (n=22) in the calcium 2-aminoethyl phosphate group received one subcutaneous injection of 20 mg/kg calcium 2-aminoethyl phosphate each day from the first day of diabetes onward.

3. The 22 animals (n=22) in the diabetic placebo group receiving 0.25 ml physiological saline each day.

The data on the changes in body weight and the amount of water drunk each day (Tab. 1) document the diabetic state of the animals in the calcium 2-aminoethyl phosphate and placebo groups: over the course of eight weeks, the diabetic animals lose about 30 g from their weight after the fasting period, while the animals in the control group gain about 100 g. The diabetic animals drink more than three times as much water as the control animals. There is no marked difference between the calcium 2-aminoethyl phosphate group and the placebo group evident from the following general metabolic parameters.

Measurements of the CV in the motor and sensory fibers of the rat tail revealed very good agreement between the groups (Tables 2a, b and c; column A in each case) in the first measurement on day 108 (before induction of diabetes), which ensures good comparability of the findings obtained subsequently. The CV in the proximal section both of the motor and of the sensory fibers, as well as in the distal part of the sensory fibers, in the control group increases markedly in the time up to the second (day 141) and up to the third (day 169) measurement (Tab. 2, columns B and C). In contrast, the CV in the diabetic placebo group remains virtually unchanged up to the second measurement and only later is a slight increase observed.

Although all the CV values in the group treated with calcium 2-aminoethyl phosphate are below the values in the control group, they do differ markedly from the values for the placebo group. In this context, the proximal section of the motor and of the sensory fibers reacts more markedly to the calcium 2-aminoethyl phosphate treatment (difference between the calcium 2-aminoethyl phosphate group and placebo group: 1.0 and 0.8, and 1.9 and 2.2) than does the distal section of the sensory fibers (0.2 and 0.6).

Statistical evaluation of the results of CV measurement on the proximal part of the caudal nerve (Tab. 3a) reveals:

1. The changes in the CV in the time from the first to the second measurement and from the first to the last measurement differ highly significantly between the control group and the diabetes groups: a diabetic neuropathy has developed in the diabetes groups.

2. The changes in the CV in the diabetic calcium 2-aminoethyl phosphate group in the time from the first to the second and from the first to the last measurement differ significantly from those in the placebo group: the severity of the developing neuropathy is significantly diminished by daily administration of calcium 2-aminoethyl phosphate.

Statistical evaluation of the results of measurement, including the less sensitive parameter of the CV in the distal section of the sensory fibers, reveals the same picture in principle, merely the difference between the calcium 2-aminoethyl phosphate group and the placebo group being significant only with $p<0.1$ for the change from the first to the second measurement, but again being $p<0.05$ for the change from the first to the third measurement.

This demonstrates that daily administration of calcium 2-aminoethyl phosphate diminishes the severity of developing diabetic neuropathy.

TABLE I

| A. Mean weight + S.E.M. (g) before and after fasting and on the days of the second and third measurements. | | | | |
|---|---|---|---|---|
| Group | n | Day 110 before fasting | Day 113 after fasting | Day 141 2nd measurement | Day 169 3rd measurement |
| Control | 14 | 262.4 + 3.3 | 235.7 + 2.7 | 309.4 + 3.5 | 336.6 + 4.4 |
| Ca 2-aminoethyl phosphate | 22 | 265.4 + 3.1 | 236.4 + 2.9 | 219.7 + 3.7 | 207.6 + 4.1 |
| Placebo | 22 | 263.8 + 2.5 | 236.2 + 1.9 | 216.7 + 2.6 | 199.2 + 3.0 |

TABLE I-continued

B. Mean daily water consumption (ml) of the animals in the control group and the two diabetes groups. S.E.M. not determined because the animals were housed in group cages.

| Group | Day 116 to 129 | Day 130 to 143 | Day 144 to 157 | Day 158 to 169 |
|---|---|---|---|---|
| Control | 20.7 | 16.8 | 17.1 | 18.0 |
| Ca 2-aminoethyl phosphate | 64.8 | 62.3 | 64.9 | 62.2 |
| Placebo | 61.9 | 62.6 | 65.9 | 64.3 |

TABLE 2

| Group | A Day 108 | B Day 141 | C Day 169 | D (B-A) | E (C-A) |
|---|---|---|---|---|---|
| A. Conduction velocity (m/s) in the proximal section of the motor nerves. | | | | | |
| Control | 29.8 + 0.6 | 34.0 + 0.6 | 35.2 + 0.5 | +4.2 + 1.0 | +5.5 + 0.8 |
| Ca 2-aminoethyl phosphate | 30.2 + 0.4 | 31.4 + 0.7 | 33.2 + 0.7 | +1.1 + 0.5 | +3.0 + 0.6 |
| Placebo | 29.4 + 0.3 | 29.5 + 0.7 | 31.6 + 0.6 | +0.1 + 0.7 | +2.2 + 0.7 |
| B. Conduction velocity (m/s) in the proximal section of the sensory nerves. | | | | | |
| Control | 38.4 + 0.4 | 42.6 + 0.5 | 45.0 + 0.5 | +4.3 + 0.4 | +6.6 + 0.5 |
| Ca 2-aminoethyl phosphate | 38.5 + 0.5 | 40.9 + 0.5 | 42.2 + 0.4 | +2.3 + 0.6 | +3.7 + 0.6 |
| Placebo | 38.7 + 0.3 | 39.1 + 0.5 | 40.2 + 0.6 | +0.4 + 0.5 | +1.5 + 0.6 |
| C. Conduction velocity (m/s) in the distal section of the sensory nerves. | | | | | |
| Control | 33.8 + 0.5 | 36.0 + 0.5 | 37.9 + 0.4 | +2.2 + 0.4 | +4.1 + 0.5 |
| Ca 2-aminoethyl phosphate | 33.5 + 0.4 | 33.4 + 0.5 | 34.4 + 0.5 | −0.1 + 0.6 | +0.8 + 0.5 |
| Placebo | 33.4 + 0.4 | 33.1 + 0.5 | 33.7 + 0.4 | −0.3 + 0.4 | +0.2 + 0.5 |

TABLE 3

Bivariant F test with 3 experimental groups. F values were calculated on the basis of the individual change in the CV in the proximal section of the motor and sensory nerves.

| Groups compared | Day 108 to 141 | Day 108 to 169 |
|---|---|---|
| Control vs. Ca 2-aminoethyl phosphate | 5.31 | 6.23 |
| vs. Placebo | 14.30 | 16.73 |
| Placebo vs. Ca 2-aminoethyl phosphate | 3.62 | 3.69 |

Degrees of freedom: df 1 = 2 and df 2 = 54. F values > 3.23 correspond to p < 0.05 and F values > 5.18 correspond to p < 0.01.

What is claimed is:

1. A pharmaceutically effective composition for the therapeutic treatment of a patient having neuropathies of the peripheral nervous system whose pathogenesis is attributable to changes in the nerve cells and which reduces the conduction velocity thereof, comprising a pharmaceutically effective amount of a compound which is selected from a group of compounds having the structural formula:

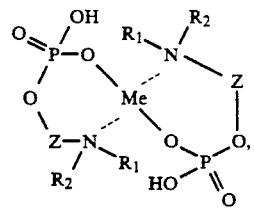

wherein Me is calcium $R_1$ and $R_2$ each means hydrogen or a lower alkyl radical (n=1, 2) or a combination of both, Z means a lower alkyl radical of straight or branched chain (n=1, 2, 3, 4) or a monocarboxylic acid (n=2, 3, 4) or a combination of alkyl radical and monocarboxylic acid, and wherein n identifies the number of carbon atoms.

2. A pharmaceutically effective composition for prophylactic treatment of a patient having neuropathies of the peripheral nervous system whose pathogenesis is attributable to changes in the nerve cells and which reduces the conduction velocity thereof, comprising a pharmaceutically effective amount of a compound which is selected from a group of compounds having the structural formula:

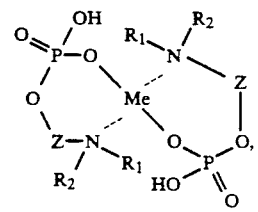

wherein Me is calcium $R_1$ and $R_2$ each means hydrogen or a lower alkyl radical (n=1, 2) or a combination of both, Z means a lower alkyl radical of straight or branched chain (n=1, 2, 3, 4) or a monocarboxylic acid (n=2, 3, 4) or a combination of alkyl radical and monocarboxylic acid, and wherein n identifies the number of carbon atoms.

3. The composition of claim 1, wherein the compound is calcium-di (2-aminoethylphosphate).

4. The composition of claim 2, wherein the compound is calcium-di (2-aminoethylphosphate).

5. The composition of claim 1, wherein the compound is calcium-di (2-N-methylaminoethylphosphate).

6. The composition of claim 2, wherein the compound is calcium-di (2-N-methylaminoethylphosphate).

7. The composition of claim 1, wherein the compound is calcium-di (2-N, N-dimethylaminoethylphosphate).

8. The composition of claim 2, wherein the compound is calcium-di (2-N,N-dimethylaminoethylphosphate).

9. The composition of claim 1, wherein the compound is calcium-di(serylphosphate).

10. The composition of claim 2, wherein the compound is calcium-di (serylphosphate).

11. The composition of claim 1, wherein the compound is calcium-di (threonylphosphate).

12. The composition of claim 2, wherein the compound is calcium-di (threonylphosphate).

13. A method of therapeutic or prophylactic treatment of a patient having neuropathies of the peripheral nervous system whose pathogenesis is attributable to changes in the nerve cells and which reduces the conduction velocity, comprising orally or intravascularly administering to the patient an effective amount of a compound which is selected from a group of compounds having the structural formula:

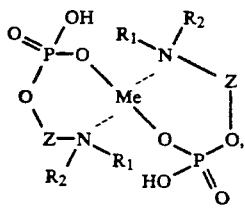

wherein Me is calcium, $R_1$ and $R_2$ each means hydrogen or a lower alkyl radical (n=1, 2) or a combination of both, Z means a lower alkyl radical of straight or branched claim (n=1, 2, 3, 4) or a monocarboxylic acid (n=2, 3, 4) or a combination of alkyl radical and monocarboxylic acid, n identifies the number of carbon atoms, and wherein said effective amount is effective for the therapeutic or prophylactic treatment of said neuropathies.

14. The method as claimed in claim 13 for the treatment of diabetic neuropathy.

15. The method as claimed in claim 13 for the treatment of alcoholic polyneuropathy.

16. The method as claimed in claim 13 for the treatment of carcinogenic polyneuropathy.

17. The method as claimed in claim 13 for the treatment of funicular spinal disease.

18. The method as claimed in claim 13 for the treatment of neuropathies following long-term therapy with cytostatics.

19. The method as claimed in claim 13 for the treatment of dysglobulinemic neuropathy.

20. The method as claimed in claim 13 for the treatment of interstitial polyneuropathy.

21. The method as claimed in claim 13 for the treatment of multiple sclerosis.

22. The method as claimed in claim 13 for the treatment of acute myelo-optic neuropathy.

23. The method as claimed in claim 13 for the treatment of demyelinating encephalopathy.

24. The method as claimed in claim 13 for the treatment of subacute sclerosing panencephalitis.

25. A method for the therapeutic or prophylactic treatment of a patient having peripheral neuropathies whose pathogenesis is attributable to changes in the nerve cells and which reduces the conduction velocity, comprising orally or intravascularly administering to the patient an effective amount of calcium-, magnesium- or zinc-di(2-aminoethylphosphate), and wherein said effective amount is effective for the therapeutic or prophylactic treatment of said peripheral neuropathies.

* * * * *